United States Patent [19]

Van Der Weerdt et al.

[11] Patent Number: 4,760,050
[45] Date of Patent: Jul. 26, 1988

[54] ISOPROPYL-METHYL-BUTENOYL-CYCLOHEXANES, -CYCLOHEXENES AND -CYCLOHEXADIENES, AND ALSO PERFUME COMPOSITIONS AND PERFUMED ARTICLES AND MATERIALS WHICH CONTAIN SAID COMPOUNDS AS A PERFUME INGREDIENT

[75] Inventors: Antonius J. A. Van Der Weerdt, Huizen; Nicolaas L. J. Broekhof; Jan G. Witteveen, both of Naarden, all of Netherlands

[73] Assignee: Naarden Intl. N.V., Netherlands

[21] Appl. No.: 2,391

[22] Filed: Jan. 9, 1987

[30] Foreign Application Priority Data

Jan. 23, 1986 [NL] Netherlands ............... 8600152

[51] Int. Cl.$^4$ ............................................. A61K 7/46
[52] U.S. Cl. .......................... 512/22; 568/376; 568/377
[58] Field of Search ............. 252/522 R; 568/376, 568/377; 512/22

[56] References Cited

U.S. PATENT DOCUMENTS

| | | | |
|---|---|---|---|
| 3,852,355 | 12/1974 | Rautenstrauch et al. | 252/522 R |
| 3,890,370 | 6/1975 | Buchi et al. | 252/522 R |
| 3,892,809 | 7/1975 | Schulte-Elte | 252/522 R |
| 3,928,456 | 12/1975 | Kovats et al. | 252/522 R |
| 4,028,278 | 6/1977 | Buchi et al. | 568/377 |
| 4,136,066 | 1/1979 | De Haan et al. | 252/522 R |
| 4,187,251 | 2/1980 | Schleppnik | 568/376 |
| 4,226,892 | 10/1980 | Kovats et al. | 252/522 R |
| 4,264,467 | 4/1981 | Schulte-Elte et al. | 512/22 |
| 4,524,020 | 6/1985 | Sprecker et al. | 252/522 R |

FOREIGN PATENT DOCUMENTS

| | | | |
|---|---|---|---|
| 0012436 | 6/1980 | European Pat. Off. | 252/522 R |
| 8600152 | 4/1973 | France | 252/522 R |
| 1240309 | 7/1971 | United Kingdom | 252/522 R |

OTHER PUBLICATIONS

Nielsen et al., "Condensation of Aldehydes with Ketones, Methylanilinomagnesium Bromide as a Condensing Agent", J. Am. Chem. Soc. 73, 4696 (1951).
R. C. Cookson et al., J. Chem. Soc. Perkin I, 1727 (1975).
"Progress in Perfumery Materials", Paul Z. Bedoukian, American Cosmetics and Perfumery, vol. 87, No. 4, Apr., 1972, pp. 27–40.
"Does Molecular Shape Determine Odor Quality?", Nature, vol. 233, Sep. 24, 1971, p. 231.
"Physicochemical Correlates of Olfactory Quality", Susan S. Schiffman, Science, vol. 185, Jul. 12, 1974, pp. 112–117.
"Olfactory Theories and the Odors of Small Molecules", Hein L. Klopping, J. Agr. Food Chem., vol. 19, No. 5, 1971, pp. 999–1004.

Primary Examiner—James H. Reamer
Attorney, Agent, or Firm—Brumbaugh, Graves, Donohue & Raymond

[57] ABSTRACT

1-Isopropyl-3-methyl-2-(but-2'-enoyl)cyclohexane derivatives having the general formula Formula 1

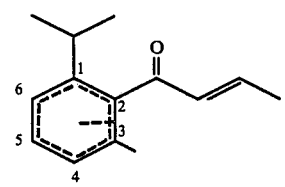

(1)

in which the dotted lines represent no double bond, one double bond at position 4 or two double bonds at positions 1 and 5, 2 and 4 or 4 and 6 are valuable fragrances with fruity flowery and green odors, in some cases accompanied by woody and/or herbal notes. Above defined compounds can be used as a perfume component in perfume compositions or in products to be perfumed.

16 Claims, No Drawings

ISOPROPYL-METHYL-BUTENOYL-CYCLOHEXANES, -CYCLOHEXENES AND -CYCLOHEXADIENES, AND ALSO PERFUME COMPOSITIONS AND PERFUMED ARTICLES AND MATERIALS WHICH CONTAIN SAID COMPOUNDS AS A PERFUME INGREDIENT

The invention relates to isopropyl-methyl-butenoyl-cyclohexanes, -cyclohexenes and -cyclohexadienes, to perfume compositions which contain one or more of said compounds as a perfume ingredient, and also to articles and materials perfumed with said compounds or with compositions containing said compounds.

There is a continuing interest in the use of synthetic fragrances in perfumes and products to be perfumed, such as cosmetics, soaps, detergents, household products, etc. This interest is stimulated by the inadequate quantity and variable quality of natural fragrances.

Surprisingly, it has now been found that 1-isopropyl-3-methyl-2-(but-2'-enoyl)cyclohexane derivatives having the general formula 1

Formula 1

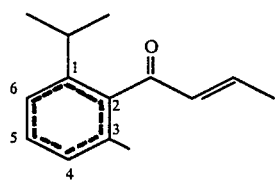

(1)

in which the dotted lines represent no double bond, one double bond at position 4 or two double bonds at positions 1 and 5, are valuable fragrances with fruity, flowery and green odours, in some cases accompanied by woody and/or herbal notes.

Many methyl-substituted butenoylcyclohexenes and -cyclohexadienes are known in the perfume industry. The great majority of these are compounds having a 1,1,3-trimethyl-2-butenoyl-substitution pattern (the numbering is as in Formula 1) and 0, 1 or 2 double bonds at positions 2, 3, 4 and 5.

The most well-known of these compounds are known as damascones and damascenones and have been detected in, inter alia, rose oil, tobacco, tea and some fruits (see, for example, British Pat. No. 1,240,309).

As a consequence of this, a large number of analogous compounds have been synthesized in which the 1,1,3-trimethyl-substitution pattern and, in particular, the two geminal methyl groups are usually retained (see, for example, U.S. Pat. Nos. 4,136,066, 3,890,370, 3,928,456, 4,226,892, 3,852,355 and 3,892,809 and the European Patent Application No. 12,436, in which compounds having two geminal methyl groups at position 1 and a methyl or methylene group at position 3, in some cases accompanied by a methyl group elsewhere in the ring, are exclusively, or almost exclusively described). The U.S. Pat. Nos. 3,928,456 and 4,226,892 also mention some compounds in which one of the two geminal methyl groups is replaced by an ethyl group. Although the U.S. Pat. Nos. 3,852,355 and 3,892,809 mention a general formula which contains the groups $R_1$ and $R_2$ at position 1 which, according to the description, may denote hydrogen or an alkyl radical containing 1-6 carbon atoms, it emerges from the further description and the examples that, in practice, $R_1$ and $R_2$ in some cases both denote hydrogen and in all the other cases both denote methyl groups.

The olfactory properties of the analogues of damascones and damascenones mentioned in the abovenamed literature are in some cases very similar to those of the last-named compounds, but in many cases are different. This is in agreement with the empirical fact that even small differences in chemical structure may often bring with them large differences in olfactory properties which are unpredictable with the present state of the art.

The compounds according to the present invention, however, have a chemical structure which differs considerably from the abovenamed known compounds and in which, in particular, the absence of the two geminal methyl groups and the presence of an isopropyl group is striking.

On the other hand, the U.S. Pat. No. 4,524,020 describes several isopropyl-methyl-substituted cyclohexylmethylketones, including 1-isopropyl-2-acetyl-3,5-dimethyl-4-cyclohexene, which primarily have a musty and musk-like odour. Quite apart from the chemical differences, the olfactory properties of said compounds thus differ considerably from those of the compounds according to the invention.

The compounds according to the invention are new and can be prepared according to methods known per se for such compounds, for example, as shown in the reaction schemes illustrated below. The Diels-Alder reaction described therein between 1,3-pentadiene and 5-methyl-3-hexen-2-one (Scheme I)

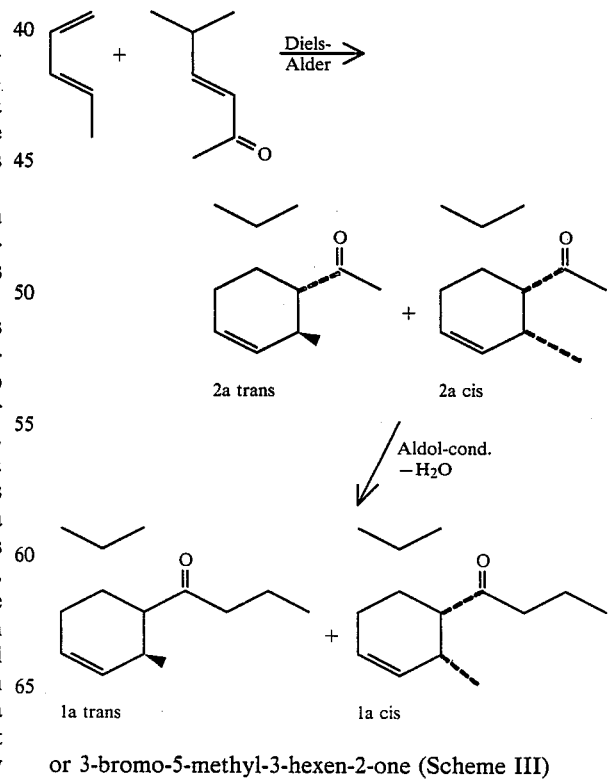

2a trans  2a cis

Aldol-cond. $-H_2O$ 1a trans  1a cis or 3-bromo-5-methyl-3-hexen-2-one (Scheme III)

Scheme III

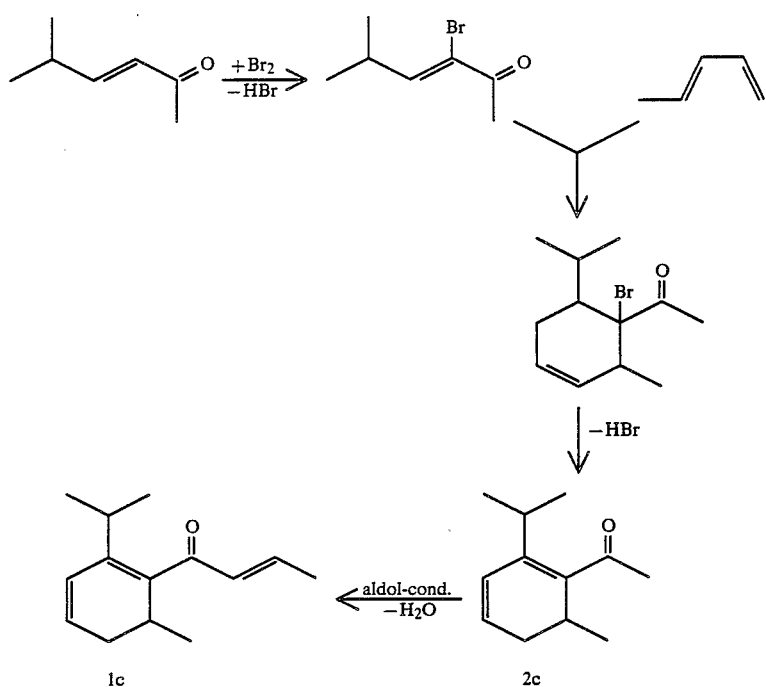

can be carried out both thermally and under the influence of a Lewis acid catalyst, for example, as described in the U.S. Pat. No. 4,524,020. Starting from trans-5-methyl-3-hexen-2-one, the two specified isomers of 1-isopropyl-2-acetyl-3-methyl-4-cyclohexene (Formula 2), which are here denoted trans and cis respectively, depending on the position of the acetyl and methyl group with respect to each other, are formed under these conditions. In said isomers the isopropyl and the acetyl group are always situated, however, on either side of the cyclohexene ring, as is shown in Scheme I. The ratio in which the two isomers are formed is dependent on the manner in which the Diels-Alder reaction is carried out. If the starting point is cis-5-methyl-3-hexen-2-one, the two corresponding isomers are obtained in which the isopropyl and acetyl groups are in the cis position with respect to each other. The isomeric 2-acetyl-1-isopropyl-3-methyl-4-cyclohexenes (2a) obtained from cis- and trans-5-methyl-3-hexen-2-one can also be converted into each other by treatment with a strong base, such as sodium methanolate or sodium hydride.

3-Bromo-5-methyl-3-hexen-2-one can be prepared according to usual methods, for example, as described by R. C. Cookson et al., J. Chem. Soc. Perkin I, 1727 (1975).

The hydrogenation shown in Scheme II is carried out in the usual manner by means of $H_2$ under the influence of known hydrogenation catalysts.

Scheme III

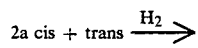

-continued
Scheme III

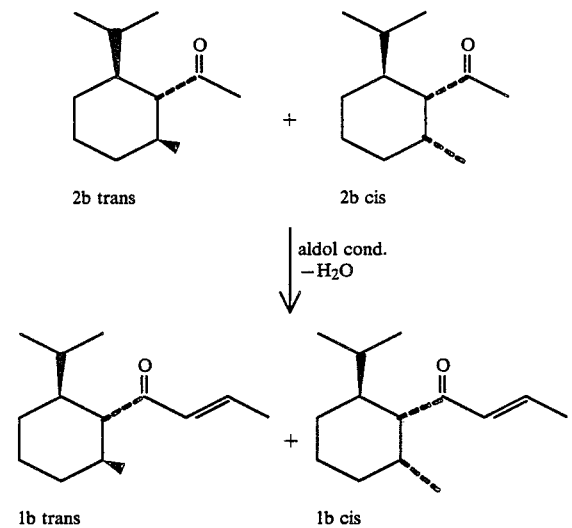

The last step of the preparation methods, shown in Schemes I–III, of the compounds according to the invention 1a–1c consists of an aldol condensation of the acetylcyclohexane derivatives 2a–2c with acetaldehyde, followed by dehydration. If said reactions are carried out under mild conditions, for example, as described by A. J. Nielsen, C. Gibbons and C. A. Zinnerman in J. Am. Chem. Soc. 73, 4696 (1951), the existing position of the substituents on the ring in the compounds 2a–2c is maintained in the end products.

As already mentioned, the compounds according to the invention are powerful and valuable fragrances, compounds 1e and the cis-trans mixture of 1a and of 1b, in particular, being notable for their presently fruity and freshly flowery odours. It has emerged that mixtures having very different cis/trans ratio hardly differ from each other in odour strength and odour character, so that an isomer separation is superfluous for use as a fragrance.

Here the term "perfume composition" means a mixture of fragrances and possibly auxiliary substances, if desired, dissolved in a suitable solvent or mixed with a powdery substrate, which mixture is used to impart a desired odour to the skin and/or products of all types. Examples of such products are: soaps, detergents, air fresheners, room sprays, pomanders, candles, cosmetics, such as creams, ointments, toilet waters, pre- and aftershave lotions, talcum powders, hair-care agents, body deodorants and anti-perspiration agents.

Fragrances and fragrance mixtures which can be used in combination with the compounds according to the invention to prepare perfume compositions are, for example: natural products, such as essential oils, absolutes, resinoids, resins, concretes, etc., but also synthetic fragrances such as hydrocarbons, alcohols, aldehydes, ketones, ethers, acids, esters, acetals, ketals, nitriles etc., including saturated and unsaturated compounds, and aliphatic, carbocyclic and heterocyclic compounds. Examples of fragrances which can be used in combination with the compounds according to the invention are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentanone, n-decanal, n-dodecanal, 9-decen-1-ol, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropine, coumarine, eugenol, vanillin, diphenyl oxide, hydroxycitronellal, ionones, methylionones, isomethylionones, irons, cis-3-hexanol and esters thereof, indan musks, tetralin musks, isochroman musks, macrocyclic ketones, macrolactone musks, ethylene brassylate, and aromatic nitro-musks.

Auxiliary substances and solvents which can be used in perfume compositions which contain compounds according to the invention are, for example: ethanol, isopropanol, diethylene glycol monethyl ether, diethyl phthalate, etc.

The quantities in which the compounds according to the invention can be used in perfume compositions or in products to be perfumed may vary within wide limits and depend, inter alia, on the nature of the product in which the fragrance is used, on the nature and the quantity of the other components in the perfume composition and on the odiferous effect which is intended. It is therefore possible to specify only very broad limits which, however, provide sufficient information for those skilled in the art to be able to use the compounds according to the invention independently. In most cases a quantity of only 0.1% by weight will already be sufficient in a perfume composition to obtain a clearly perceptible odiferous effect. On the other hand, to achieve special odiferous effects, it is possible to use quantities of 25% by weight or even more in a composition. In products perfumed by means of perfume compositions, these concentrations are proportionately lower, depending on the quantity of the composition used in the product.

The following examples serve only to illustrate the preparation and use of the compounds according to the invention. The invention is, however, not limited to them.

EXAMPLE I

Preparation of 1-isopropyl-3-methyl-2-(but-2'-enoyl)-4-cyclohexene (a) Diels-Alder reaction A solution of 67.2 g (0.6 mol) of trans-5-methyl-3-hexen-2-one in 300 ml of cyclohexane was added dropwise to 19.8 g (0.15 mol) of $AlCl_3$ in 900 ml of cyclohexane in the course of 45 minutes while stirring, the mixture being cooled in ice-water.

The mixture was then heated to approx. 60° C. and a solution of 156 g (2.3 mol) of piperylene in 300 ml of cyclohexane was added dropwise in the course of 2 hours, after which the reaction mixture was stirred for a further 2.5 hours at said temperature. After cooling, the reaction mixture was poured out onto a mixture of 1,200 g of ice and 300 ml of concentrated hydrochloric acid. The acidic water layer was separated off and extracted once with 300 ml of cyclohexane. The organic layers collected were washed consecutively with 300 ml of 10% hydrochloric acid, 300 ml of water, 300 ml of saturated $NaHCO_3$ solution and 300 ml of saturated NaCl solution and dried over $MgSO_4$. The solution was evaporated down and the residue distilled. 72 g of the cis-trans mixture of 2-acetyl-1-isopropyl-3-methyl-4-cyclohexane (2a), b.p. 50° C./13 Pa, were obtained.

(b) Aldol condensation

An ethyl magnesium bromide solution was prepared from 11.2 g (0.47 mol) of magnesium and 60 g (0.55 mol) of ethyl bromide in 500 ml of diethyl ether. A solution of 43 g (0.40 mol) of N-methylaniline in 150 ml of benzene was added to this solution while stirring in the course of 30 minutes at approx. 25° C., and the mixture was stirred for 20 minutes under reflux and then cooled in ice to 15° C., after which a solution of 63 g (0.35 mol) of 2-acetyl-1-isopropyl-3-methyl-4-cyclohexene in 150 ml of benzene was added dropwise while stirring at said temperature in the course of 2 hours. The reaction mixture was stirred for a further hour at 15° C. and then cooled to −15° C., after which a solution of 17.6 g (0.40 mol) of acetaldehyde in 150 ml of benzene was added dropwise at said temperature in the course of 1 hour. The reaction mixture was stirred for a further hour at said temperature, after which it was allowed to rise to approx. +10° C., stirring all the time. It was then poured out into a mixture of 500 g of ice and 150 ml of concentrated hydrochloric acid.

The acidic water layer separated off was extracted twice with 150 ml of ether, after which the organic layers collected were washed consecutively with 150 ml of 10% hydrochloric acid, 150 ml of ice-water, 150 ml of saturated $NaHCO_3$ solution and 150 ml of saturated NaCl solution. The organic solution was dried over MgSO₄ and evaporated down. The evaporation residue (86 g) was taken up in 500 ml of toluene, with 3.5 g of oxalic acid being added, and heated to reflux while stirring for 4 hours, the water formed being separated off with a Dean-Stark apparatus. The organic solution was then washed with saturated NaHCO₃ solution and with saturated NaCl solution and dried over MgSO₄. The solution was evaporated down and the residue distilled. The distillate was fractionated in a 40-cm Vigreux column, 77 g of a mixture of trans- and cis-1-isopropyl-3-methyl-2-(but-2'-enoyl)-4-cyclohexene (1a) being obtained, trans/cis ratio=1:7; b.p. 77° C./10 Pa; $n_D^{20}$=1.4950.

NMR (100 MHz, CCl₄, δ in ppm with respect to TMS):

trans 1a: 0.76 (3H, d, J=7 Hz); 0.85 (3H, d, J=7 Hz); 0.88 (3H, d, J=7 HZ), 1.4–2.6 (6H); 1.91 (3H, d d, J=7 Hz, J=1.5 Hz); 5.38 (1H, d with fine structure, J=10 Hz); 5.60 (1H, d with fine structure, J=10 Hz); 6.18 (1H, d qu, J=15 Hz, J=1.5 Hz); 6.82 (1H, d qu, J=15 Hz, J=7 Hz).

cis 1a: 0.63 (3H, d, J=7 Hz); 0.76 (3H, d, J=7 Hz); 0.89 (3H, d, J=7 Hz); 1.4–2.2 (4H); 1.90 (3H, dd, J=7 Hz, J=1.5 Hz); 2.38 (1H, m); 2.86 (1H, m); 5.56 (2H); 6.05 (1H, d qu, J=15 Hz, J=1.5 Hz); 6.76 (1H, d qu, J=15 Hz, J=7 Hz).

The mixture had a pleasant, fruity-flowery odour reminiscent of apple and rose with a slight minty note in the after-smell.

EXAMPLE II

Preparation of 1-isopropyl-3-methyl-2-(but-2'-enoyl)-1,5-cyclohexadiene (1c)

(a) Preparation of 3-bromo-5-methyl-3-hexen-2-one

A solution of 84 g of bromine in 75 ml of CCl₄ was added dropwise to a mixture of 42 g of NaHCO₃ and 56 g of 5-methyl-3-hexen-2-one in 175 ml of CCl₄ at 0° C. while stirring in the course of 2 hours. The reaction mixture was stirred for a further hour at 0° C. and then filtered off and evaporated down. The residue was taken up in 150 ml of a 1:1 mixture of ethanol and water, to which 63 g of NaHCO₃ had been added. The mixture was heated to reflux while stirring for 2 hours. After cooling, it was poured out into ice-water. This mixture was extracted three times with pentane. This extract was washed twice with water, dried over MgSO₄, filtered off and evaporated down. The residue was distilled, 41 g of 3-bromo-5-methyl-3-hexen-2-one (E) being obtained, b.p. 62°–82° C./2 kPa.

(b) Diels-Alder reaction

This was carried out as mentioned in Example I, starting from 72 g of AlCl₃ in 300 ml of cyclohexane to which 41 g of bromomethylcyclohexenone in 100 ml of cyclohexane were added, followed by 27 g of piperylene in 100 ml of cyclohexane. After working up and distilling, 28.5 g of 2-acetyl-2-bromo-1-isopropyl-3-methyl-1-cyclohexene, b.p. 62°–82° C./20 Pa, were obtained.

This was dissolved in 100 ml of dimethylformamide and added dropwise in the course of 1 hour at 120° C. to a solution of 14.8 g of Li₂CO₃ and 5.2 g of Lif in 100 ml of dimethylformamide, the reaction mixture being stirred and kept under a nitrogen atmosphere. The mixture was stirred for a further 2 hours at 120° C. and after cooling, was poured out into 600 ml of ice-water. The aqueous mixture was extracted three times with 150 ml of pentane. The pentane extracts collected were washed twice with water and once with saturated NaCl solution, dried over MgSO₄ and evaporated down. The residue was distilled, 14.7 g of 2-acetyl-1-isopropyl-3-methyl-1,5-cyclohexadiene (2c) being obtained, b.p. 45°–50° C./13 Pa.

(c) Aldol condensation

This was carried out as specified in Example I, starting from 0.09 mol of ethyl magnesium bromide in 150 mol of diethyl ether, to which the following were added consecutively: 9.2 g of N-methylaniline in 50 ml of dry benzene, 13.4 g of 2-acetyl-1-isopropyl-3-methyl-1,5-cyclohexadiene in 50 ml of dry ether and 3.8 g of acetaldehyde in 50 ml of dry ether. After working up, the condensation product was taken up in 125 ml of toluene and dehydrated under the influence of 1 g of oxalic acid as also described in Example I. The reaction mixture obtained in this process was worked up and the crude product fractionated, 11.2 g of 1-isopropyl-3-methyl-2-(but-2'-enoyl)-1,5-cyclohexadiene (1c), b.p. 61°–63° C./26 Pa, being obtained.

NMR (100 MHz, CCl₄, in ppm with respect to TMS): 0.94 (3H, d, J=7 Hz); 0.94 (3H, d, J=7 Hz); 0.96 (3H, d, J=7 Hz); 1.93 (3H, dd, J=7 Hz, J=1, 5 Hz); 2.4–2.8 (3H); 2.92 (1H, m); 5.60 (2H); 6.08 (1H, d qu, J=15 Hz, J=1.5 Hz); 6.72 (1H, d qu, J=15 Hz, J=7 Hz).

The compounds had a pleasant fruity-flowery and somewhat woody odour with green and herbal notes in the after-smell.

EXAMPLE III

Preparation of 1-isopropyl-3-methyl-2-(but-2'-enoyl)cyclohexane (1b)

36 g of 2-acetyl-1-isopropyl-3-methyl-4-cyclohexene (2a), obtained by the Diels-Alder reaction according to Example I, were dissolved in 200 ml of ethanol and hydrogenated in the presence of 1 g of 5% Pd/C at 20° C. in the course of 30 minutes under a hydrogen pressure of 300 kPa. The catalyst was then filtered off, the filtrate evaporated down and the residue distilled. The product obtained (35 g, b.p. 50° C./13 Pa) was then subjected to an aldol condensation with acetaldehyde as described in Example I. After dehydration and working up, the crude reaction product was fractionated, 34 g of a mixture of cis- and trans-1-isopropyl-3-methyl-2-(but-2'-enoyl)cyclohexane (1b) being obtained; b.p. 70° C./13 Pa; $n_D^{20}$=1.4858; trans/cis ratio 1:7.

NMR (100 MHz, CCl₄, δ in ppm with respect to TMS); 0.66 (3H, d, J=7 Hz); 0.77 (3H, d, J=7 Hz); 0.88 (3H, d, J=7 Hz); 1.3–2.0 (8H); 1.88 (3H, dd, J=7 Hz, J=1.5 Hz); 2.08 (1H, m); 2.68 (1H, dd, J=10 Hz, J=4 Hz); 6.04 (1H, d qu, J=15 hz, J=1.5 Hz); 6.74 (1H, d qu, J=15 Hz, J=7 Hz).

The mixture had a pleasant greenish flowery and somewhat herbal odour, with a light woody note reminiscent of tobacco in the after-smell.

EXAMPLE IV

A rose perfume was prepared according to the recipe below:

| | |
|---|---|
| phenylethyl alcohol | 465 parts by weight |
| geraniol | 100 parts by weight |
| citronellol | 100 parts by weight |
| rosana NB | 50 parts by weight |
| phenylethyl acetate | 40 parts by weight |
| trirosol | 30 parts by weight |
| geranium oil | 30 parts by weight |

| -continued | |
|---|---|
| undecen-10-al* | 25 parts by weight |
| oil of cloves | 20 parts by weight |
| phenylacetaldehyde dimethylacetal | 20 parts by weight |
| hydroxycitronellal | 20 parts by weight |
| undec-10-en-1-ol* | 20 parts by weight |
| Ylang-oil | 10 parts by weight |
| benzyl acetate | 10 parts by weight |
| citronellyl acetate | 10 parts by weight |
| cinnamyl alcohol | 10 parts by weight |
| nonan-1-ol* | 10 parts by weight |
| methylphenyl acetate | 5 parts by weight |
| α-ionone | 5 parts by weight |
| isobutylsalicylate | 5 parts by weight |
| musk tincture | 5 parts by weight |
| mixture from Example I | 10 parts by weight |
| TOTAL | 1,000 parts by weight |

*10% solution in dipropylene glycol. Instead of the mixture from Example I, it was possible to use the mixture from Example III or compound 1e from Example II successfully.

We claim:

1. A perfume composition comprising fragrance materials and an effective odorant amount of at least one fragrancing compound of the formula 1

Formula 1

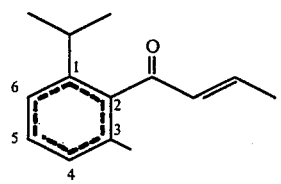

(1)

in which the dotted lines denote no double bond, one double bond at position 4 or two double bonds at positions 1 and 5.

2. A perfume composition according to claim 1 comprising an effective odorant amount of at leasrt one fragrancing compound of the formula 1, in which the dotted lines denote no double bond, one double bond at position 4 or two double bonds at positions 1 and 5.

3. A perfume composition according to claim 1 comprising at least 0.1% by weight of the compound of the formula 1.

4. A perfumed product comprising an effective odorant amount of at least one fragrancing compound of the formula 1

Formula 1

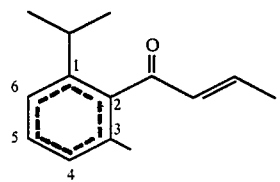

(1)

in which the dotted lines denote no double bond, one double bond at position 4 or two double bonds at positions 1 and 5.

5. Compounds of the formula 1,

Formula 1

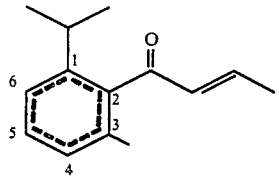

(1)

in which the dotted lines denote no double bond, one double bond at position 4 or two double bonds at positions 1 and 5.

6. Perfume composition as in claim 1 comprising an effective odorant amount of at least one compound selected from the group consisting of 1-isopropyl-3-methyl-2-(but-2'-enoyl)-4-cyclohexene, 1-isopropyl-3-methyl-2-(but-2'-enoyl)-1,5-cyclohexadiene, and 1-isopropyl-3-methyl-2-(but-2'-enoyl)-cyclohexane.

7. Perfume composition as in claim 1 comprising an effective odorant amount of a mixture of one part trans-1-isopropyl-3-methyl-2-(but-2'-enoyl)-4-cyclohexene and seven parts cis-1-isopropyl-3-methyl-2-(but-2'-enoyl)-4-cyclohexene.

8. Perfume composition as in claim 1 comprising an effective odorant amount of 1-isopropyl-3-methyl-2-(but-2'-enoyl)-1,5-cyclohexadiene.

9. Perfume composition as in claim 1 comprising an effective odorant amount of a mixture of one part trans-1-isopropyl-3-methyl-2-(but-2'-enoyl)-cyclohexane and seven parts cis-1-isopropyl-3-methyl-2-(but-2'-enoyl)-cyclohexane.

10. Perfumed product as in claim 4 comprising an effective odorant amount of at least one compound selected from the group consisting of 1-isopropyl-3-methyl-2-(but-2'-enoyl)-4-cyclohexene, 1-isopropyl-3-methyl-2-(but-2'-enoyl)-1,5-cyclohexadiene, and 1-isopropyl-3-methyl-2-(but-2'-enoyl)-cyclohexane.

11. Perfumed product as in claim 4 comprising an effective odorant amount of a mixture of one part trans-1-isopropyl-3-methyl-2-(but-2'-enoyl)-4-cyclohexene and seven parts cis-1-isopropyl-3-methyl-2-(but-2'-enoyl)-4-cyclohexene.

12. Perfumed product as in claim 4 comprising an effective odor amount of 1-isopropyl-3methyl-2-(but-2'-enoyl)-1,5-cyclohexadiene.

13. Perfumed product as in claim 4 comprising an effective odorant amount of a mixture of one part trans-1-isopropyl-3-methyl-2-(but-2'-enoyl)-4-cyclohexane and seven parts cis-1-isopropyl-3-methyl-2-(but-2'-enoyl)-4-cyclohexane.

14. 1-isopropyl-3-methyl-2-(but 2'-enoyl)-4-cyclohexene.

15. 1-isopropyl-3-methyl-2-(but-2'-enoyl)-1,5-cyclohexadiene.

16. 1-isopropyl-3-methyl-2-(but-2'-enoyl)-cyclohexane.

* * * * *